US00PP28012P2

(12) United States Plant Patent
Hansen

(10) Patent No.: US PP28,012 P2
(45) Date of Patent: May 9, 2017

(54) ***TIARELLA* PLANT NAMED 'FINGERPAINT'**

(50) Latin Name: ***Tiarella* hybrid**
Varietal Denomination: Fingerpaint

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 14/998,969

(22) Filed: Mar. 10, 2016

(51) Int. Cl.
*A01H 5/02* (2006.01)

(52) U.S. Cl.
USPC ..... Plt./486

(58) Field of Classification Search
USPC ..... Plt./486
See application file for complete search history.

*Primary Examiner* — Annette Para

(57) ABSTRACT

The new hybrid plant cultivar of *Tiarella* 'Fingerpaint' has light pink flower buds developing into white flowers on dense branched panicles in spring above palmately-lobed leaves that have a blotchy, burgundy, center palm surrounded by jade. Leaves develop to dark greyed-purple in winter. The loose mound is vigorous growing and semi-running.

1 Drawing Sheet

Botanical denomination: *Tiarella* hybrid.
Cultivar designation: 'Fingerpaint'.

BACKGROUND OF THE INVENTION

The present invention relates to a new and distinct cultivar of foamflower in the Saxifragaceae family and given the cultivar name of 'Fingerpaint'. *Tiarella* 'Fingerpaint' resulted from a cross between *Tiarella* 'Pink Brushes' U.S. Plant Pat. No. 13,329, as the female or seed parent and *Tiarella* K11-14-03, an unreleased proprietary hybrid, as the male or pollen parent. The new plant was hybridized by the inventor on Jan. 17, 2012, sown on Feb. 14, 2012 and initially selected from among other seedlings growing at a nursery in Zeeland, Mich. in the summer of 2012 and ultimately given the breeder code 12-05-2. *Tiarella* 'Fingerpaint' has been asexually propagated by division and by careful tissue culture propagation at the same nursery in Zeeland, Mich., and the resultant asexual propagules have been remained stable, true to type and exhibit the same characteristics as the original plant in multiple generations.

No plants of *Tiarella* 'Fingerpaint' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

BRIEF SUMMARY OF THE INVENTION

The nearest comparison varieties known to the applicant are the parents, *Tiarella* K11-12-17 (not patented) and *Tiarella* K11-14-03. 'Fingerpaint' has a more rounded and crenate lobe apices with darker and broader maroon-purple palm in the leaf center than both parents.

Compared to *Tiarella* 'Jade Peacock' U.S. Plant patent application Ser. No. 14/120,514, 'Fingerpaint' has more rounded and crenate lobe apices and darker and broader maroon-purple palm in the leaf center. The habit of 'Fingerpaint' is also looser and slightly more running in the landscape than 'Jade Peacock' U.S. Plant Pat. No. 26,730 while being more compact and less running than *Tiarella* 'Running Tapestry' Not Patented.

*Tiarella* 'Fingerpaint' is distinct from all other foamflower plants known to the applicant in the following combined traits:

1. Light pink flower buds densely displayed on numerous branched panicles.
2. Loose mounded habit with numerous panicles through spring period.
3. Moderate to deeply lobed palmate foliage with slightly glossy surfaces.
4. Foliage color with center burgundy palm surrounded by light green to jade green becoming tinted with greyed-purple in winter.
5. Foliage with crenate margins and rounded lobe apices.

BRIEF DESCRIPTION OF THE DRAWINGS

The photographs of *Tiarella* 'Fingerpaint' demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
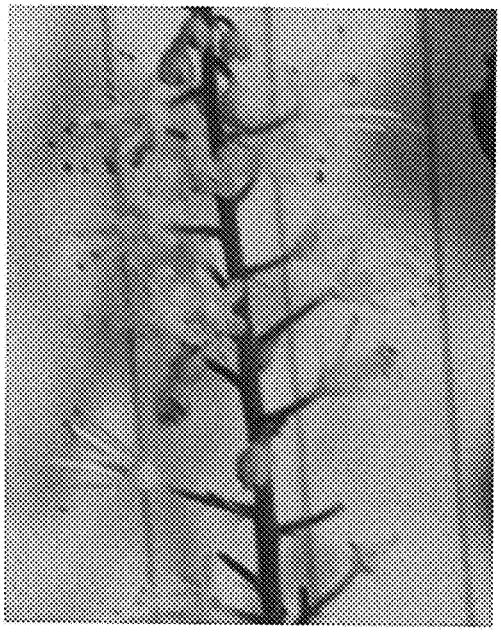
FIG. 1 shows a close-up of the flowers and buds of the new plant in spring.
Figure 2:
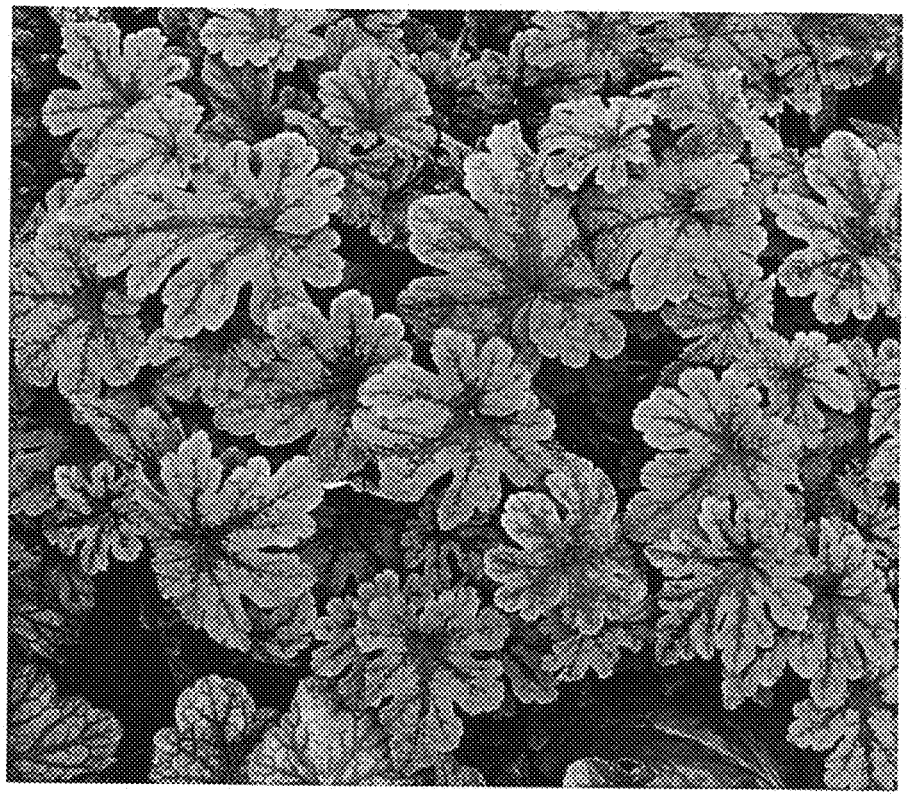
FIG. 2 shows a close-up of the foliage of the new plant in mid-summer with various stages of foliage colors.

The following description is based on a three-year-old plant of *Tiarella* 'Fingerpaint' growing in a partially shaded trial garden with supplemental water and fertilizer in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female (seed parent) *Tiarella* 'Pink Brushes' U.S. Plant Pat. No. 13,329; male (pollen) *Tiarella* K11-14-03.

Plant habit: Hardy herbaceous perennial with lose mounded habit with basal shoots each with a basal rosette of foliage; mounded foliage to about 22.5 cm tall and about 42.0 cm in diameter.

Roots: Fibrous, finely branched; color light beige to near white depending on soil type.

Growth rate: Rapid, rooting from cutting in 2 weeks and finishing in three-liter container in about 3 months.

Foliage: Palmately quinque-lobed; serrate to crenate; hirsutulous above and below; slightly lustrous above and below.

Leaf blade: To about 10.0 cm long and 8.0 cm wide, average about 9.0 cm long and about 7.2 cm across; incised to about 2.5 cm, average about 1.2 cm; indentations shallow; flat surface to lightly concave downward.

Leaf blade color: Seasonably slightly variable; spring young emerging leaves adaxial surface nearest RHS 144A with botching concentrated around major veins of between RHS N186B and RHS N186C, abaxial between RHS 144A and 144B between veins and blotching concentrated around major veins of between RHS N186B and RHS N186C; mature leaves adaxial surface nearest RHS N144C near margins and between veins with concentrated blotching around veins of between N186B and RHS N186C, abaxial surface between RHS 144A and RHS 144B around margins and between veins with the center concentrated blotching nearer RHS N186C than RHS N186B; early fall developing broadening blotching around veins of adaxial surface between RHS N186B and RHS N186C and between RHS 174C and RHS N167C toward margins with majority of leaf between margin and maroon purple veins nearest RHS 146A; abaxial broadening of blotching around veins to between RHS N186C to RHS N186B, margins becoming nearest RHS 167D to RHS 165D; winter adaxial nearest RHS 187A and abaxial nearest RHS 195A with slight tinting of RHS 182B.

Leaf margin: Hirsutulous, serrate as young emerging leaf and becoming crenate in maturity.

Leaf apex: Acute becoming rounded in maturity.

Leaf base: Cordate with overlapping lobes.

Leaf surface: Hirsutulous both above and below.

Leaf quantity: About 100 per plant.

Veins: Palmate; hirsutulous adaxial and abaxial; adaxial slightly impressed, abaxial costate.

Vein color: Nearest RHS 160D on adaxial mature leaves developing a strong tinting of nearest RHS N186C in winter; secondary adaxial veins same color as surrounding tissue all seasons; main abaxial nearest RHS 160 most of growing season and in winter developing to nearest RHS 195A with slight tinting of RHS 182B; secondary abaxial veins between RHS 137 A and RHS 189A through all seasons.

Petiole: Terete, hirsute, about 10.0 cm long and 2.0 mm diameter.

Petiole color: Nearest RHS 145A developing tinting of nearest RHS 183B in cold weather.

Inflorescence: Compact, lightly-branched panicle; about 30 to 35 racemes per plant in mid-spring; about 60 flowers per main stem, lower branches with about 6 flowers per branch and branches toward middle of panicle with two to four flowers; about 2.5 cm across; individual racemes flowering starting in early May for about 4 weeks.

Fragrance: Sweetly fragrance.

Peduncle: Terete, hirsute, about 27.0 cm tall and 2.0 mm in diameter; attitude upwards.

Peduncle color: Distal portion nearer RHS 182B than RHS 182A; middle portion and lower nearest RHS 146C.

Pedicel: Terete, hirsutulous, about 4.0 mm long and 0.7 mm diameter.

Pedicel color: Nearest RHS 183D.

Buds: One day prior to opening-oblong, about 3.0 mm long and 2.0 mm diameter; glandular.

Bud color: Apex nearest RHS 65D and darkening proximally to between RHS 65C to RHS 65B at base.

Flower: Perfect, actinomophic, petaloid sepals, rotate, with stamens exserted, about 5.0 mm long and 6.0 mm in diameter at face; individual flowers lasting about 4 days on plant or on cut panicle; attitude horizontal.

Petals: Five; glabrous; spatulate; margin entire, apex narrowly acute, base attenuate; about 2.5 mm long and 1.2 mm wide.

Petal color: White, nearest RHS N155D on both surfaces.

Calyx: Five sepals; glabrous adaxial, glandular abaxial; campanulate; oblong-ovate, acute apex; fused in the basal about 1.0 mm; about 2.5 mm long and 1.5 mm across.

Sepal color: Adaxial white, lighter than RHS 155D; abaxial lighter than RHS N155D when opened.

Androecium: Typically ten.

*Filaments*.—Thin, exserted, about 5.0 mm long and less than 0.5 mm diameter; color white, lighter than RHS 155D.

*Anthers*.—Elliptic; longitudinal, basifixed; about 0.7 mm long and 0.5 mm diameter; color nearest RHS 26A prior to dehiscing.

*Pollen*.—Abundant; color nearest RHS 31A.

Gynoecium: Carpels two, unequal.

*Style*.—Two, separate; 0.5 and 2.5 mm long and about 1.0 across; lighter than RHS 155D.

*Stigma*.—Miniscule; same color as style.

*Ovary*.—Oblong with pointed apex; about 2.0 mm long and 1.0 mm diameter; color nearest RHS 1D.

Fruit: Two-valved capsule, about 6 mm long and 3 mm in diameter at widest portion; color nearest RHS 199A.

Seed: Ovoid, less than 0.3 mm long and wide; color nearest RHS 200A.

Disease and pest tolerance: The new plant grows best with ample moisture and drainage in some shade. As with most foamflower plants, 'Fingerpaint' is usually avoided by browsing deer. Cold hardy and heat tolerant from USDA zones 4 to 9. Other resistance and tolerance beyond that normal for *Tiarella* has not been observed.

I claim:

1. The new and distinct foamflower plant named *Tiarella* 'Fingerpaint' as herein described and illustrated.

* * * * *